(12) United States Patent
Alfano (10) Patent No.: US 9,168,223 B2
(45) Date of Patent: Oct. 27, 2015

(54) CUSTOM-PILL COMPOUNDING SYSTEM WITH FILLER-FREE CAPABILITY

(71) Applicant: Kenneth Mimnaugh Alfano, Canton, MI (US)

(72) Inventor: Kenneth Mimnaugh Alfano, Canton, MI (US)

(73) Assignee: Tailorpill Technologies, LLC, Canton, MI (US)

( * ) Notice: Subject to any disclaimer, the term of this patent is extended or adjusted under 35 U.S.C. 154(b) by 356 days.

(21) Appl. No.: 13/757,828

(22) Filed: Feb. 3, 2013

(65) Prior Publication Data

US 2013/0149377 A1 Jun. 13, 2013

Related U.S. Application Data

(63) Continuation of application No. PCT/US2011/062167, filed on Nov. 26, 2011.

(60) Provisional application No. 61/426,576, filed on Dec. 23, 2010.

(51) Int. Cl.
*A61K 9/00* (2006.01)
*A61J 3/07* (2006.01)
*G05D 11/13* (2006.01)

(52) U.S. Cl.
CPC ............ *A61K 9/0087* (2013.01); *A61J 3/074* (2013.01); *G05D 11/134* (2013.01)

(58) Field of Classification Search
CPC ..... A61J 3/074; A61K 9/0087; G05D 11/132; G05D 11/133; G05D 11/134
USPC ............ 141/83, 100–105, 144–147; 424/451
See application file for complete search history.

(56) References Cited

U.S. PATENT DOCUMENTS

| | | | |
|---|---|---|---|
| 5,597,995 A | | 1/1997 | Williams |
| 5,855,233 A | * | 1/1999 | Bolelli ........................ 141/144 |
| 5,965,167 A | | 10/1999 | Sanghvi |
| 5,971,037 A | * | 10/1999 | Ansaloni ...................... 141/83 |
| 6,901,972 B1 | * | 6/2005 | Nelson ........................ 141/67 |
| 6,923,979 B2 | | 8/2005 | Fotland |
| 6,962,715 B2 | | 11/2005 | Lee |
| 6,985,798 B2 | | 1/2006 | Crowder |
| 7,140,403 B2 | * | 11/2006 | Gamberini .................... 141/83 |
| 7,284,574 B2 | * | 10/2007 | Fontaine et al. ............... 141/72 |
| 7,404,968 B2 | | 7/2008 | Abrams |
| 7,462,365 B2 | | 12/2008 | Costantino |

(Continued)

FOREIGN PATENT DOCUMENTS

| | | |
|---|---|---|
| JP | 2005-046420 | 2/2005 |
| WO | WO-A-01/33176 | 5/2001 |

OTHER PUBLICATIONS

Published International Search Report (ISR) the ISA for PCT/2011/062167, ISA/KR.

(Continued)

*Primary Examiner* — Timothy L Maust (57) ABSTRACT

A system and associated aspects thereof are disclosed regarding custom-compounding of drug products such as pills and polypills for particular patients, herein involving adaptations of "micro-dosing" technology to permit sufficiently small and precise amounts of drug substances or optionally formulations thereof to be controllably and automatably handled and dispensed so as to help create customized drug products that do not necessitate bulking or dilution of the drug substances.

10 Claims, 4 Drawing Sheets

(56) References Cited

U.S. PATENT DOCUMENTS

| | | | |
|---|---|---|---|
| 7,536,843 B2* | 5/2009 | Djurle et al. | 53/502 |
| 7,574,844 B2 | 8/2009 | Kamineni | |
| 7,707,964 B2 | 5/2010 | Childers | |
| 7,727,576 B2 | 6/2010 | Figueroa | |
| 7,912,582 B1 | 3/2011 | Holtje | |
| 8,074,835 B2* | 12/2011 | MacMichael et al. | 222/1 |
| 8,479,784 B2* | 7/2013 | Goldman et al. | 141/144 |
| 8,914,148 B2* | 12/2014 | Wagner | 700/240 |
| 2003/0010791 A1 | 1/2003 | Gentiluomo | |
| 2004/0004085 A1 | 1/2004 | Williams | |
| 2004/0172169 A1* | 9/2004 | Wright et al. | 700/265 |
| 2005/0129746 A1 | 6/2005 | Lee | |
| 2006/0000470 A1 | 1/2006 | Clarke | |
| 2007/0087048 A1 | 4/2007 | Abrams | |
| 2007/0087049 A1 | 4/2007 | Clarke | |
| 2008/0017669 A1 | 1/2008 | MacMichael | |
| 2008/0142277 A1 | 6/2008 | MacMichael | |
| 2008/0190801 A1 | 8/2008 | Kwok | |
| 2009/0014086 A1 | 1/2009 | MacMichael | |
| 2009/0149507 A1 | 6/2009 | Kirsh | |
| 2009/0175936 A1 | 7/2009 | Röhr | |
| 2009/0232886 A1 | 9/2009 | Sison | |
| 2010/0015184 A1 | 1/2010 | Tuel | |
| 2010/0100391 A1 | 4/2010 | Daya | |
| 2010/0158956 A1 | 6/2010 | Komorowski | |
| 2011/0229530 A1 | 9/2011 | Gazzaniga | |
| 2012/0029030 A1 | 2/2012 | Kirsh | |
| 2012/0041778 A1 | 2/2012 | Kraft | |
| 2012/0145806 A1 | 6/2012 | Yang | |

OTHER PUBLICATIONS

"Informal Comments" responding to the ISR for PCT/2011/062167 (uploaded by Applicant to IB via "ePCT").

Xcelodose(R) S / Capsugel, "Introducing the New Xcelodose(R) S", 2008, http://capsugel.com/media/library/xcelodose_s_precision_powder_micro_dosing_system.pdf.

Published International Search Report (ISR) by the ISA for PCT/2011/062167, ISA/KR.

\* cited by examiner

CUSTOM-PILL COMPOUNDING SYSTEM WITH FILLER-FREE CAPABILITY

CROSS-REFERENCE

This filing is a US continuation application claiming priority to international patent application PCT/US2011/062167, filed on Nov. 26, 2011, which claims priority to U.S. provisional application 61/426,576, filed on Dec. 23, 2010, both of which are hereby incorporated by reference in their entireties.

FIELD

This application relates to medical devices, and more particularly, relates to automated compounding of customized drug products, along with methods for usage and implementation.

BACKGROUND

This section provides background information related to the present disclosure, which is not necessarily prior art - especially the selection, emphasis, and combination of and commentary on matters discussed. Separate and distinct topics addressed for background in this section include: 1) the traditional and current practice of pharmaceutical "compounding," 2) benefits and challenges of combination drugs or "polypills," whether manufactured or compounded, 3) "inkjet" based dispensing approaches for customizing drug oral dosage forms, and 4) current "micro-dosing" technologies for expediting manufacturability of pills for clinical trials.

Pharmaceutical "compounding" is when a pharmacist prepares medication uniquely for a particular patient, based on a physician's prescription. Before the prevalence of mass-produced drugs, this was a very common practice, but now it has largely been relegated to special cases where a mass-produced version of a drug is either unavailable or unsuitable for a patient. Provided that each compounded medication is uniquely prepared for an individual patient pursuant to a physician's order, compounding generally falls outside the jurisdiction of the FDA and instead within the regulation of the practice of Pharmacy under relevant state law. This line is not always clear, but there is strong general support for maintaining the flexibility needed to personalize medication at the pharmacy level and likewise not unduly bias physicians towards prescribing mass-produced products or dosage levels. But if the "compounding" is not for just one patient/customer but prepared in anticipation of multiple similar prescriptions, it may cross the line into "manufacturing" —and thus subject to such regulations.

Most compounding is either manual or partially-automated with the help of certain tools or equipment. So-called Automated Compounding Devices (ACDs), having full automation, exist at this time only for parenteral/intravenous (I.V.) medications, which are prepared as comparatively high-volume liquid solutions administered from bags (typically in a hospital). There is a noteworthy distinction between "reconstitution" which is performed according to a manufacturer's instruction versus "compounding" which is performed according to a doctor's prescription. Compounding of solid oral dosage forms is relatively rare today for several reasons, including the time and skill involved compared to the relative logistical ease of using mass-produced products instead.

"Polypills" or "combopills" are pills (capsules or tablets) containing multiple medications, manufactured to have combinations and dosages that would get prescribed together. For example, one particular "5-in-1 polypill" is targeted for heart-disease patients and it contains three blood pressure medications, a cholesterol reducer, and aspirin. Polypills are not presently common - especially for more than two drugs - partly because each permutation of drugs and dosages to be marketed must first be developed (including blends with appropriate inactive ingredients), trialed (for a suitable population), FDA-approved, manufactured, and stocked. To be worthwhile for a drug manufacturer, a particular drug/dosage permutation would need to prove suitable for a large number of people. Hence, manufactured polypills lack much personalizability. (In fact, even single-drug pills typically have very limited dosage options.) Alternatively, personalized polypills are possible via custom-compounding by a pharmacist, but very few pharmacies offer such service as it requires significant skill and time and current means have various challenges (e.g. precision, waste, etc.). Hence, combopills/polypills are simply not utilized much today, despite their potential to aid with the prevalent phenomenon of polypharmacy.

Much research has been done over many years on the potential to use inkjet printing based technologies for producing oral drug dosage forms, which may have applicability for facilitating patient-customized pills or polypills, including with customized formulations; Hewlett-Packard has published and patented significantly on inkjet-related approaches (e.g. U.S. Pat. Nos. 6,962,715, 7,727,576, and 7,707,964), which can offer precision and accuracy for spraying or jetting liquid drops of fluid API-in-solution onto an ingestible substrate such as a sheet or film, as well as for facilitating layer-by-layer deposition of powder substances (which is useful in making controlled-release tablets, via binding agents for "3-dimensional printing." Ink-jet principles have also been adapted for dispensing liquid drugs into vials, or onto porous tablet substrates. All such ideas have been suggested to offer benefits for R&D, mass production, and customized dosage forms -including for multiple drugs. However, their dispensation is restricted to liquids, and to work with capsules they require an intermediary substrate.

In another development which is wholly unrelated to compounding or polypills, there have emerged some technologies to aid the manufacturability of new drugs for clinical trials. To manufacture drug capsules for clinical trial patients, traditionally this had required a choice between either developing a formulation with appropriate excipient(s) to permit automated manufacture (which was not precise enough to accurately handle raw drug substance without bulking), or else manually weighing the active pharmaceutical ingredient (API) for each capsule (requiring much time and skill, especially for potent substances). In recent years, certain manufacturing equipment has solved this dilemma and thus expedited many candidate drugs' manufacturability.

In order to allow automated manufacture without needing to develop a formulation, certain capsule filling machines have been developed which possess ability for "micro-dosing" very small amounts of powder with great precision, speed, and reliability. These are utilized to place raw API directly into capsules, in order to postpone the need to develop blends until initial studies can be done. This can save several months of delays before trials, thereby allowing failures to occur faster and with less sunk-cost. Simple formulations or select excipients can be included as well when desired, which may still involve significantly less mass than would otherwise be needed without micro-dosing. The most successful of such systems have used a "pepper-shaker" means (e.g. U.S. patent applications Ser. Nos. 11/571,169 and 12/035,037).

For example, the "Xcelodose" line of products by Capsugel can produce "API only" capsules - thus enabling sooner human trials without needing to first develop a formulation or perform compatibility or preformulation studies. Precise "micro-dosing" or "micro-filling" can be accurate to 100 micrograms-being of API directly, or in simple formulation (if preferred), or after treatment such as bulk densification or compaction (which may occasionally be needed), with minimal waste/attrition owing partly to the lack of a powder bed. Sometimes pre-processing steps (e.g. milling) may enhance performance but are not typically needed; other optional features for potential enhancement can include humidity control or thin metal prongs/baffles to minimize agglomeration. Also, capsule type/size and powder properties can vary significantly. Other systems featuring similar capability, using significantly different technological means, are available from other companies: Mettler-Toledo has the "Quantos" and Symyx has the "Powdernium," which employ other precision-dispensing mechanisms. Known usage and exploitation of all such capabilities has only extended to research and development (R&D) applications & clinical trial product manufacturing-and only for single-drug products.

SUMMARY

This section provides a brief general summary of the disclosure, and is not a comprehensive disclosure of the invention's scope or features.

The present invention involves an automated compounding device, and associated processes and methods, for compounding solid and other encapsulated medications as prescribed for individual patients. The degree of automation can vary, and can be semi-automated. Critical aspects of the inventive items and processes herein include precision micro-dosing technology, which enables very small amounts of drug substance to be reliably and accurately dispensed without requiring non-therapeutic diluent, and adaptation of the same to receiving and executing patient-specific information so as to constitute "compounding" rather than "manufacturing," thus requiring the ability to perform small discrete runs with appropriate drug changes and operational differences between each.

Applications include, for example, facilitating extemporaneous production of custom-prescribed polypills in pharmacies (e.g., hospital, retail, or mail-order). Another application is facilitating compounding of single-drug pills whose manufacture (and thus availability) is limited by such things as niche/low demand, shortage, lack of regulatory approval, or difficulty formulating in a "manufacturable" form. Moreover, for both single and multi-drug capsules, an application includes facilitating customized dosage levels (beyond the mass-produced options, which are typically very limited). These applications could in turn facilitate the use of compliance-packaging, and potentially reduce medication error, by reducing pill-burden.

Further inventive details and areas of applicability will become apparent from the description provided herein. The description, drawings, and examples in this specification are intended for purposes of illustrative purposes only and are not intended to limit the scope of the present disclosure.

DRAWINGS

The drawings described herein are for illustrative purposes only and are not intended to limit the scope of the present disclosure, as countless versions of many aspects of the present inventive devices and methods are possible. These example drawings, in combination with the detailed description, collectively convey sufficient knowledge to those in the art.

FIG. 1 is an example of a simple and generalized conceptual-relational diagram of a polypill-capable micro-dosing compounding system. It features a base unit comprising micro-dosing capsule-filling instrumentality as a central component of the overall system 105 which allows the inputs of patient information via user interface 101 and ingredient substances 104 via various possible logistical approaches to result in the output of said patient's pills 106 being produced in the specified quantity. Appropriately programmed software 102 could feasibly reside in various locations and it controls a plurality of dispensing mechanisms such as heads 103 which are operationally integrated with each other as well as said central instrumentality. Optional integrated accessories 107 may facilitate the system itself processing select ingredient material(s) among other functions. Capsule shells are not shown, but would of course be an input also.

The remaining figures depict a particular example compounding system for dispensing multiple powder APIs into capsules using the "salt/pepper-shaker" approach, to illustrate some possible ways to achieve some of the necessary adaptations. In this case, each dispensing head (which also serves as a cartridge holding each respective API/blend) is manually placed in the machine for each prescription run. Capsule shell bottoms are also manually placed, and later capped and removed when filled. Automated features include activation of the solenoid for tapping the dispensing head to release powder therefrom, and motors to selectively rotate the dispensing head holder and to incrementally advance the pill rack (not shown). While this system could designate which pills did not satisfy specifications, such as by hole-number in the pill rack, disposal therefrom would be manual here. And when a cartridge is nearing empty, which could be programmed to be inferred via lengthening fill times, the operator could be prompted through the user interface to manually exchange it. (Note that many of the adaptations for small patient-specific runs may render the manual roles inherent in this example design less onerous than they would be in a manufacturing application.)

Specifically, in FIG. 2 there is an overall view of such a system, including a monitor for display 201, a keyboard 202 for entry or retrieval of information such as a given patient's drug(s) and dosage(s), and a casing 203 with internal components of the dispensing mechanism. A separate cartridge tray 204 holds dispensing heads/cartridges not being used in a given run.

In this case, the number of holes built into the rotor perimeter represents the maximum number of distinct ingredients that can be used in any given run, and the number of places in the pill rack represents the maximum number of pills that can be produced in any given run. Note that some features are shown with apparent liberties taken for conceptually illustrative purposes. Operationally, each ingredient could be put into each capsule before advancing to the next capsule, or vice-versa, however the latter may be preferable to minimize movement of dispensing heads while their bottom-holes are exposed. The dimensions and capacities (and any variations therein) of the cartridges/heads would of course affect the dimensions of the rotor, casing, etc. Materials can also vary significantly.

DESCRIPTION

Figure 1:
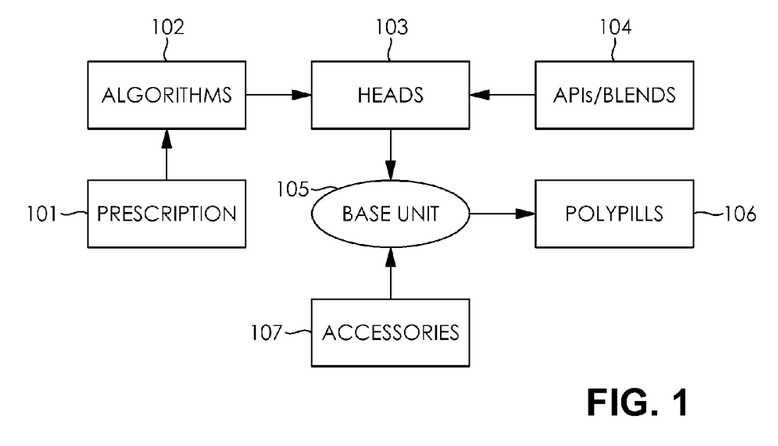
Figure 2:
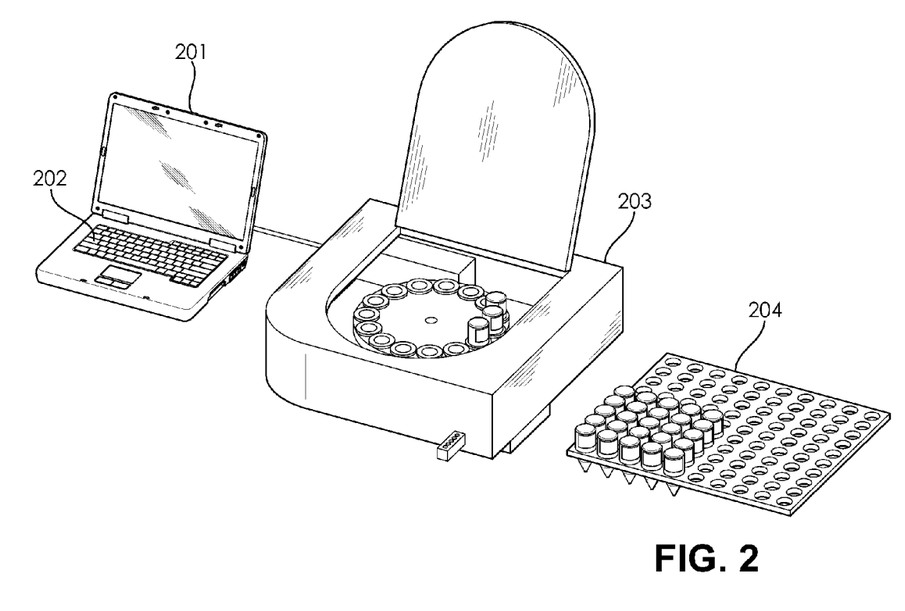
Figure 3:
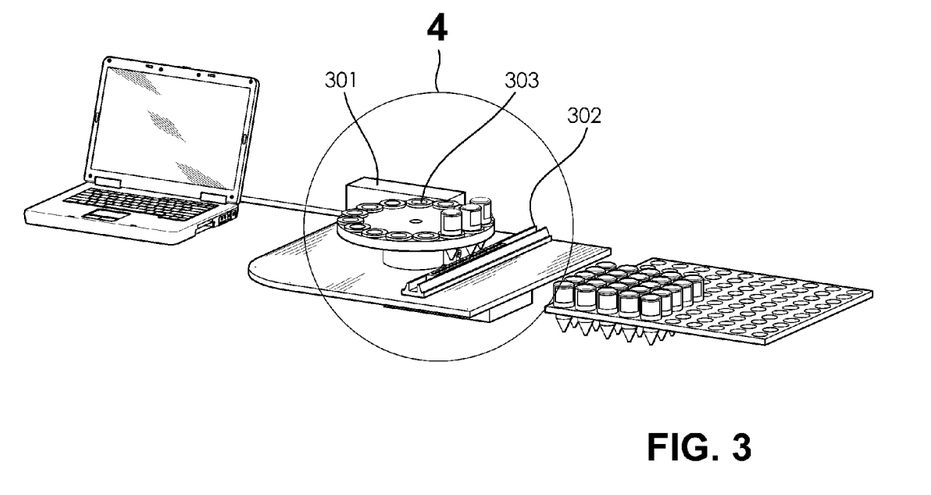
FIG. 3 shows a view of this same system without the casing to reveal the central processing unit or CPU 301, a pill rack tray 302, and a rotor to hold and position dispensing heads/cartridges 303.
Figure 4:
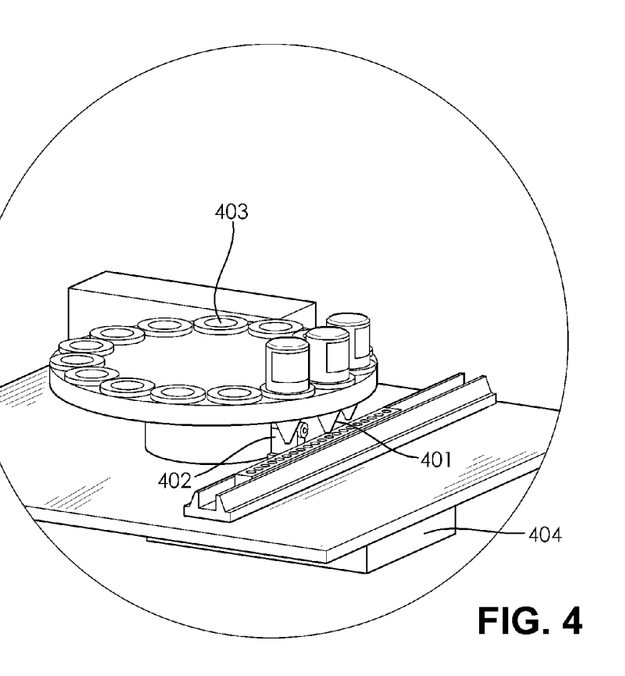
FIG. 4 zooms further to show the tips of dispensing heads 401, the solenoid 402 having a pointed rod to tap the head, rubber padding 403 to isolate vibration from other heads not being tapped, and a highly-sensitive scale or micro-balance such as a Zeta scale 404 under the capsule being filled to provide continuous feedback during filling to influence the rate of tapping.
Figure 5:
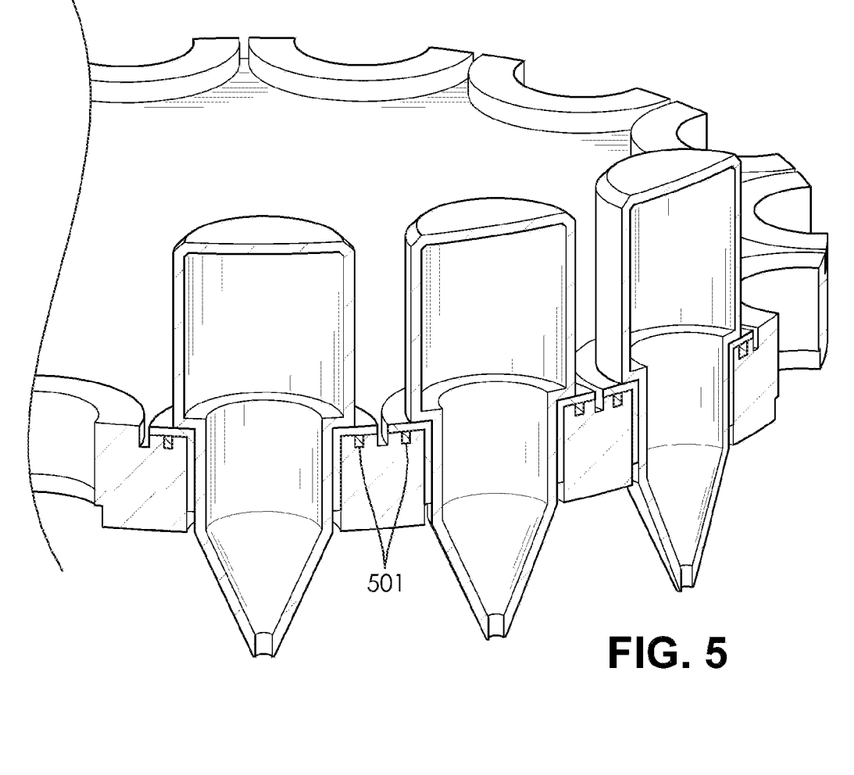
FIG. 5 shows a cross-sectional cutaway of a dispensing head secured to the rotor via magnets 501 built in to the rotor holder and configured to pull and hold the head against said rubber padding with sufficient force to be stable without being so tight as to defeat the isolative function of the rubber padding.
Figure 6:
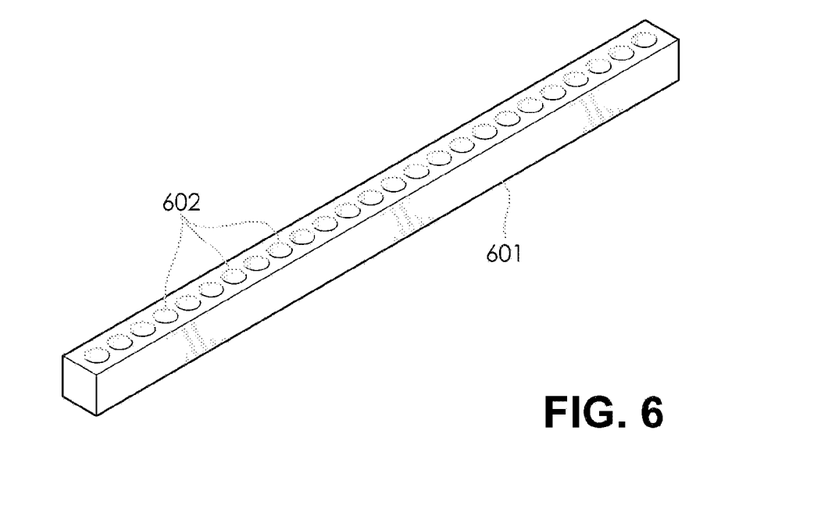
FIG. 6 shows a pill rack 601 which slides within in said pill rack tray, and which contains enough holes 602 for a particular prescription run.
Figure 7:
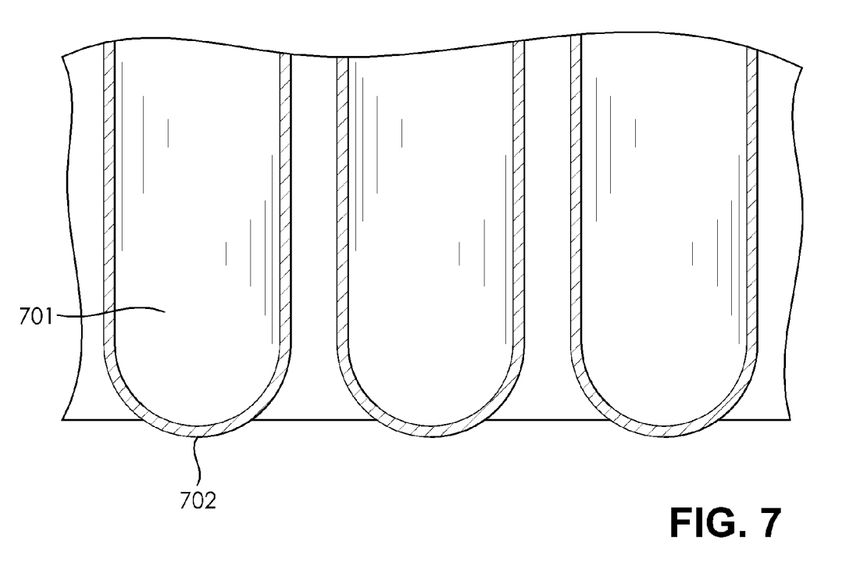
FIG. 7 shows a cross-sectional cutaway of a portion of the pill rack tray in order to show how example capsule pieces 701 may fit therein. Moreover, in this particular configuration, the curvature of the capsule shell bottom 702 is exploited as it partially protrudes through a comparatively smaller hole in the bottom of the pill rack (not large enough in diameter to let the full capsule fall through), which in turn facilitates weighing each pill from below—as the rack slides/advances between capsules going over the scale.

Important characteristics and example embodiments are provided so that this disclosure will be thorough, and will convey the full inventive scope to those who are skilled in the art. Because of the infinite conceivable variations of the system and its features and uses, example approaches are provided for some prominent aspects with the understanding that these can be combined in many permutations, especially with the contextual guidance provided explicitly and implicitly herein. It will be apparent to those of ordinary knowledge of existing relevant technologies that some details need not be employed, that some attributes may be embodied in many different forms, and that neither should be construed to limit the scope.

The present invention encompasses an automated compounding system, and associated methods and processes and their components and products, for compounding encapsulated medications (typically orally administered). This facilitates and expands accessibility of personalized single- or multi-drug pills tailored to individual patient needs, beyond what is available presently.

Embodiments of the invention combine the principle of pharmaceutical compounding with the technology of precision micro-dosing capsule-filling (including "API-only" capability) which currently exists only in drug research/development applications where it is utilized to delay or reduce the need for a formulated version during Phase 1 & 2 clinical trials. Embodiments comprise any degree of automation, semi- or full. (Today there are semi-automated capsule-filling instruments available to compound pills but without precision micro-dosing, and there are fully-automated compounders for parenteral/intravenous fluid.) Some embodiments involve augmenting micro-dosing capsule-filling equipment to enable multiple APIs (alone or blended; raw or treated) being placed into the same capsules.

While most embodiments of the present invention are expected to be for solid-form APIs, the invention encompasses embodiments for semi-solid (i.e. lipid-based, poorly water-soluble compounds) and some fluidic dispensation means applicable to capsule filling-as well as associated sealing/encapsulation means and applications for the output produced. Likewise, most embodiments are expected to be for non-biological ("small-molecule") drugs, however, some biopharmaceuticals are feasible to incorporate-such as peptides/proteins suitable for oral delivery via appropriate formulations under development capable of preventing enzymatic degradation in vivo, and overcoming their unique obstacles to dissolution and intestinal permeation. Furthermore, while the primary uses and benefits of the invention are expected to focus on human patients, many concepts are readily adaptable to analogous veterinary applications (where legally permitted).

The ability to avoid the need for diluents (also sometimes known as "fillers" or "bulking agents"), and in the case of powder APIs avoid also the need for solvent-abilities made possible by the micro-dosing/insertion features presently being directed at clinical-trial pill manufacture-is a critical aspect of making it feasible and practical to have automated compounding of multi-drug polypills and/or personalized-dosage pills. For example, grinding tablets to put into capsules would be prohibitively voluminous for many polypills, and likewise for using powder blends that fail to omit much unnecessary material. (Often such "non-functional" excipients are used now to facilitate handling, measuring, manufacturability, controllability, etc.—and a significant part of their role is to add volume or mass.) This is partly because of the space-saving consequences of limiting unnecessary content (which at least increases the room for additional APIs or blends), along with the reduced need for usage or validation of formulations, reduced waste, and the net overall reduction of ingredient processing and preparation. By contrast, pharmacologically functional excipients such as surfactants and disintegrants, or stability-enhancing or inter-substance barrier excipients, or even glidants or lubricants (not needed for the preferred embodiments of the present invention) could add relatively little mass or volume and thus can still be usefully employed where appropriate. Of course, any remaining free space in a capsule may optionally be filled with diluent if desired.

Broad system and method embodiments cover means or steps for compounding by dispensing API or formulation into capsules in sufficiently small and exact quantities as to substantially eliminate need for non-therapeutic diluent, along with articles of their input and output-such as refillable or replaceable cartridges of source material, and pills packaged for enhancing patient adherence. Also encompassed is optional inclusion of accessory features to help blend API with excipient on-demand if preferred (which may make higher automation preferable), or to process or treat API where desired. Note that powder blends—whether pre-blended or not-might best be granulated in a manner selected to ensure against segregation, depending upon the ingredients involved and the mechanical dispensation approach employed. Embodiments may involve adapting suitable existing or future micro-dosing or capsule-filling means, or incorporating their design features (some of which may themselves have proprietary aspects and/or additional supplemental benefits).

Existing technical approaches found in today's automated capsule-filling machines may be incorporated-such as disposable dispensing heads, RFID chips to facilitate actuation or data storage, mechanical shock waves or channeled pins for actuating dispensation, or opening/closing a valve while a whist turns in the hopper. Other features could include metering screws, feedback algorithms for coordinating microbalance readings with iteratively-adjusted dispensing actuations, robotic workstations with selectable source and destination modules, among countless other attributes. Such operational principles can be adapted directly from existing micro-dosing machines such as by Capsugel ("Xcelodose"), Mettler-Toledo ("Quantos"), and Symyx ("Powdernium"), employing electro-mechanical pharmaceutical technology known in the art.

In particular, the "salt/pepper-shaker" style of approach to dispensation found in such systems today typically involves an actuated arm or rod tapping at a dispensing head to cause micro-scale quantities of powder to fall upon being tapped, while a feedback loop tracks the mass dispensed as sensed by a microbalance which continuously monitors accumulating mass in a capsule (note that some microbalances are available which could have sufficient sensitivity to weigh an entire pill tray or rack holding a small batch of capsules, relying upon tarring and computation to discriminate); key variables with this approach include the number and/or size of holes at the bottom of a head and the number and/or force of the tap impacts (which can be sourced from a solenoid). Assuming the holes are reasonably well suited to the powder substance, between each tap impact against the dispensing head a fairly predictable quantity will fall quickly and then be stopped by the formation of powder "micro-bridges" until the subsequent tap. Because of the smaller runs involved with compounding compared to manufacturing, these variables can potentially be calibrated for optimal accuracy at the expense of speed-which may involve smaller holes and lighter taps (in addition to a more sensitive balance, which can be obtained accurate to 0.001 mg). The rate of tapping can be adjusted via iterative closed-loop feedback in response to the tracked progress toward filling with respect to the target mass to be dispensed; this real-time capability enables powders of various flow characteristics to be accommodated, although theoretically the tap rate could potentially be held constant if it were slow enough to ensure against overfill (although that could be prohibitively slow in many cases).

This general principle could be adapted in many ways for compounding, provided that a system is configured for discrete runs by both hardware (e.g. means for changing or selecting drug(s) for each use, while avoiding cross-contamination; a multiplicity of dispensing mechanisms for each pill, in the case of multi-drug pills) and software (e.g. an interface to receive patient-specific information on drug(s)/dosage(s); algorithm modifications, in the case of multi-drug pills, for directing multiple drugs to the same pills).

Embodiments may comprise adaptations of relevant technology to facilitate dispensing multiple APIs (and/or other ingredients) into the same capsules, for compounding of "polypills," by extrapolating or varying the design principles currently used for non-compounding applications. (For example, in capsule-filling equipment for R&D applications, double/triple and double-filling options exist on some products; also, some automated dispensers are "many-to-many" (source-to-destination), "one-to-one" or "one-to-many.") Some feasible ways to adapt current powder micro-dosing design principles toward multi-drug capability involve coordinating multiple dispensing arms and heads, for multiple frequently-used APIs/drugs, some of which could remain on "stand-by" during any given prescription when not among the APIs being selected-for embodiments where supplies of all available ingredients need not be loaded by the operator between every use. This could be arranged such that the chosen heads travel to each capsule-or vice versa. With these approaches, a microbalance weighing the capsules being filled may provide only an aggregate reading for total accumulated content dispensed, hence the feedback algorithm might also continuously calculate the subset of weight attributable to each additional drug being dispensed in succession (or re-tare between). Additional coordination and control algorithms could be included to handle issues of sequence management, non-interference, etc. Many such engineering adaptations are possible, with varying degrees of complexity but with comparable feasibility as for many similar electro-mechanical pharmaceutical devices (optimal applications of which are routinely guided by consultation with relevant cognate fields such as pharmacology, pharmaceutics, and pharmacy.)

Some embodiments may not require as large of a capacity as the high-throughput machines now directed at clinical trials; in fact, the inherently individualized nature of compounding often favors lower-scale devices, which may also be more logistically and spatially favorable for many pharmacy settings. Such adjustments can be an aspect of adapting the relevant technology for the small discrete runs associated with "compounding" (vs. "manufacturing"). Likewise, the degree of automation employed may vary. Unlike manufacturing drug product for clinical trials (where high automation enhances throughput for any given pill to be produced), when compounding drug product for individual patients the advantages of automation are less focused on necessarily maximizing throughput, given the clinical and legal constraints on production batch sizes for such purposes, which nicely allows for prioritization of more relevant mechanisms such as for multi-API capability.

Device embodiments comprise interfaces for directly or indirectly entering prescription information in a manner conducive to pharmacy practice, likely integrated with the software operating the machine, possibly including an ability to interface with the pharmacy's computer system or information technology (IT) network, such as for processing prescriptions sent electronically. Interfaces may be analog or digital, manual or automatic, hardware or software, etc., and may even comprise standard computer products such as desktop or notebook or tablet style (however, some internal intelligence, e.g. data acquisition, would likely still be needed for non-interface purposes). Alternatively, an integrated touch-screen on the device casing is an option. Countless sorts of such interfaces are readily feasible to suit any desired degree of sophistication, and the information they receive may vary depending on the extent of system automation (for example, a largely-manual system may only require dose levels corresponding to cartridge positions, if the pharmacist/technician is responsible ensure the corresponding drug's cartridge is placed accordingly). And depending on the governing laws and regulations of pharmacy practice, prescription information entered for a given set of polypills for a given patient may not need to all come from a single prescription or a single physician (i.e., if pharmacists are permitted to combine separate prescriptions).

There is also an opportunity to add a computerized checkpoint for inter-drug compatibility or counter-indications (this requires access to an appropriate database for cross-reference). Even if a particular patient requires multiple pills (or multiple polypills), assuming these are all produced by the same system and managed by the same pharmacy, then there is still the potential to incorporate such monitoring. This does assume that the system is aware of which drugs are being dispensed, rather than having the pharmacist/operator simply designate dosages by cartridge position.

As an additional safety and/or proprietary measure, source housing containers could be readable or recognizable by the system in order to enable it to ascertain drug identity; currently adoptable options for achieving this include RFID tags, bar-coding, or direct-contact sensors. These electronic approaches, as well as mechanical fittings or the like, could also help to preclude connection or utilization of non-authorized drug source containers.

Note that for either single or multi drug compounding, API(s) must be able to be selected (and/or swapped-out, as needed), either manually or via automation, more readily than with R&D or clinical-trial manufacturing, as this should be doable between every customer/patient. Relatedly, this must also avoid cross-contamination among different drugs-especially for embodiments that involve operator swapping of drugs on-demand, to accommodate a wider selection than the system itself can access at any given time. These are aspects of optimizing the technology for small discrete runs, which is important in making the transition from manufacturing to "compounding." Various such adaptations are feasible, and the particular approaches should vary depending upon the kind of micro-dosing or capsule-filling technologies chosen. For example, one approach for these matters, when using the "salt/pepper-shaker" type of powder dispenser, can employ exchangeable dispensing heads which also serve as ingredient-supply cartridges that the operator of the system manually places into the machine according to each patient's prescription. Dispensing heads could additionally be optimized for each respective ingredient's properties, as is done with existing micro-dosing equipment in manufacturing contexts. (Such an embodiment would only accommodate a fixed number at once, likely corresponding to the number of different ingredients (APIs, blends, excipients) that could be placed into each capsule, while an unlimited number of exchangeable cartridges could be stored separately.

As noted, embodiments may comprise integrated components or accessories for processing or formulating APIs, when desired. Some powder APIs might simply be marketed in blended or granulated form for direct use in these systems, in the event that select functional excipients may be useful for pharmacokinetic reasons or for intra/inter-drug stability. Moreover, when the machine does excipient blending on-demand, there is no reason why this could not also be personalized (e.g. selection, ratios, etc.), although principal benefits of this invention include customizing selection of drug and dosage level. Conversely, certain particle sizes/ranges or granularities for particular source APIs or blends may be specified in protocols or instructions. Embodiments can also comprise housing containers or cartridges, refillable or disposable (or reusable/recyclable), for distributing input powders to pharmacies and for attaching/interfacing them with the compounders. Where a containment cartridge is also serving as a dispensing head, and the "salt/pepper-shaker" method is being used, the holes on the bottom of the heads can be capped when not in use; an alternative way to achieve this objective is to incorporate an inverse pattern that can slide or twist as needed to cover/uncover the holes.

Embodiments may comprise placing barriers between APIs that should not be in contact within capsules (i.e. for inter-drug stability concerns in vitro). One way to achieve intra-capsule separation is a "capsule-in-capsule" approach: preparing a small capsule containing those API(s) to be segregated from the other(s), for subsequent insertion into a larger capsule containing said other(s). This would require a machine amenable to varying capsule sizes (and perhaps capsule substances), and could incorporate a mechanism for automated insertion of the smaller capsule into the larger capsule-performed along with API-dispensing into the larger capsule. Micro-encapsulated API particles may instead provide separation on the particle-level, and could also be utilized to achieve sustained/delayed release characteristics if desired. (Note that controlled-release or inter-drug separation might be achieved inherently if excipient blending or granulation is employed for some simple formulation-e.g., a lactose, starch, microcrystalline cellulose, etc. Alternatively, delayed-release and/or multi-compartment capsules could be used.) Such possibilities could also help control taste, when capsules are expected to be re-opened for consumption rather than being swallowed whole. Embodiments may use current or later-developed means of achieving sufficient separation, such as exploiting hydrophobicity/hyrdophilicity, microcapsules, or nanoparticles.

System embodiments may be scaled or reconfigured to accommodate different demands, priorities, budgets, or preferences. For example, some embodiments may be limited to a pre-determined set of APIs to be readily accommodated, or be accessorized so as to potentially accommodate a wide or flexible range of APIs. Loading of APIs or blends can be done directly (either manually or automated), or facilitated via interfacing cartridges or the like. Likewise, embodiments may require loading/attaching such cartridges before each use, or be equipped to have select standard drug cartridges remain attached until depleted; similarly, whether or not a dispensing head stores significant amounts of API is a variable parameter, as is whether or not the dispensing head is disposable or reusable, or serves also as the cartridge.

Inventive processes and methods associated with the system include compounding encapsulated medication personalized to patients pursuant to their respective drug(s) and dosage(s). Implementation methods include usage of custom polypills for outpatients with high pill-burden, including compliance packaging for outpatients, as well as hospital or long-term-care inpatients—for whom medication dispensation and administration errors occur in correlation to the quantity and frequency of medication.

Another related use is in conjunction with blister-packing or the like (which is often required for pills of nursing-home patients) or other unit-dose packaging or even specialized dispensing apparatuses; or, in the case of health-system pharmacies, the small plastic packets/pouches that hold one or more pills designated for inpatients (often with printed labeling on the outside). Note that inpatients' drugs and dosages are often not "settled" and can thus change often, so adaptation there would require having low pill quantities per machine run.

Embodiments may comprise adaptations, variations, or improvements of existing semi- or fully-automatic devices now directed at R&D—including powder form (e.g. Xcelodose), or liquid/semi-solid form (e.g. CFS) via means not requiring a substrate (unlike with inkjet approaches). Embodiments can comprise other current or future means of achieving sufficiently precise placement of material into capsules. Some modes and aspects of current or future functional means or features could themselves be proprietary and/or provide additional benefits complementing or building upon the present invention.

A preferred embodiment of the system and associated operating method comprises select principles of operation being adapted from Capsugel's Xcelodose 600S (fully-automated) machine for powder APIs/blends. A gravimetric dispensing system featuring a highly sensitive micro-balance along with rapid and precise metering/aliquotting technology ("Precision Powder Microdosing System"), it employs a predictive control algorithm to accomplish both very high speeds of dispensation as well as dynamic actuation adjustment to accommodate in real-time a wide range of powder/granule/bead properties or characteristics (e.g. "sticky" or cohesive vs. free-flowing; hygroscopic/humidity-sensitive, lyophilized, micronized etc.). In its current applications of R&D/ trials, this model rectifies, opens, fills, and closes 10× faster than manually. Some key adaptations would include appropriately reconfigured hardware and software engineered for compounding individual prescriptions on demand-such as accommodating readily changeable API(s), short/discrete runs, and individual information entry. Other changes would enable dispensing multiple APIs/formulations into the same sets of capsules, via extrapolating existing design principles and adding adequate integration intelligence for enabling automated polypill compounding. Also preferred is to utilize multiple disposable and replaceable cartridges, with each housing one input drug or excipient or formulation substance, which as discussed above would also require avoidance of cross-contamination between discrete uses if an exchanged source is permitted to be of a different ingredient (with one way to achieve this being to dispense directly from the cartridge). Changes to the graphical user interface (GUI) would of course require patient-specific features such as described above, while retaining its ability to stipulate acceptance criteria (for determining which capsules of a batch fall outside of specifications, which are thus rejected automatically).

For liquid or semi-solid formulations, suspensions, or emulsions-a currently preferred embodiment would comprise similarly appropriate adaptations of features associated with Capsugel's CFS line (with its proprietary "Liquid-Encapsulation Micro-spray Sealing" system), which combines filling and sealing and doses accurately from 0.1 ml, among various other features.

A preferred embodiment of the immediate output of the system and methods, where applicable, is a capsule containing multiple drugs of patient-customized selection and dosage, some of which may be pure API while some may be wet- or dry-granulated blends, encapsulated particles, or microspheres. A preferred embodiment of the eventual ultimate output of the system and methods herein, for nursing-home patients or hospital outpatients having high pill-burden, is compliance-package blister-packs designating a single pill to be taken at particular time(s) or with a particular meal(s) each day. The latter requires combined implementation with appropriate packaging equipment.

Some notable advantages which help to elucidate how to target and apply the invention include (without limitation) enabling more pharmacies to offer prescription-compounded capsules suited to individual patients (by requiring less time and skill), thereby expanding access to personalized drug dosages and combinations thereof such as via customized polypills-with resultant benefits to patient convenience, compliance, and health. This can facilitate adherence to multi-drug regimens, whether for different conditions or combination therapy for a single condition. When using powder-form drug substances with unsealed or re-openable capsules, this also facilitates subsequent mixing or dissolving the dispensed powder with food or drink or other solvent; note that this could require a non-adhesive interface between capsule and contents, which may require anti-static treatment and/or appropriate excipients. And in contrast to inkjet methods, the invention notably entails the ability to custom-compound by placing pharmaceutical materials into capsules without necessarily requiring first dissolution into solvent and deposition onto a substrate/sheet.

One safety application and benefit especially applicable to hospitals or long-term care facilities or the like is the potential to reduce inpatient medication errors (particularly dispensation or administration errors pertaining to incorrect drugs or dosages, including omission and wrong-dose and wrong-time errors) by significantly reducing the number of pills needing to be administered, handled, etc., which is a significant factor in medication error risk. Medication errors among highly-medicated patients have been documented to account for many injuries and costs. High rates of medication errors in assisted-living facilities and the like occur with the following medication classes: cardiovascular, anti-convulsant, anti-psychotic, anti-infective, anti-platelet, anti-diabetic, laxative, anti-hyperlipidemic, anti-depressant, and others. And as mentioned previously, there is also potential to have drug-drug interactions (DDI) checked for or flagged during compounding of a given polypill prescription, thereby reducing downstream risk of mis-combination when taken separately.

Regarding outpatients, important applications involve patient compliance, and thus safety, as patient noncompliance among high pill-burden patients has been documented to account for many injuries and costs. High pill-burden outpatient groups often include transplant, HIV, cancer, mental-health, and others. Extensions of the drug-consolidation potential of polypills include, for example, the ability to prescribe two separate polypills (perhaps using labeled capsules) for morning and night, with compatible medications being clustered and incompatible medications separated for patient safety (certain drugs could also overlap between them). Another variation on this could include four daily polypills-in conjunction with "compliance packaging" or the like-as some highly medicated patient groups require multiple medications with breakfast, lunch, dinner, and at bedtime. (Of course, such packaging could also be useful for nursing home inpatients, where blister-packing is often a legal requirement.) Furthermore, select niche patient groups may be targeted who are at unique risk of error (e.g., blind patients).

An additional niche application/advantage lies in being able to gradually increase or decrease a patient's dosage of any particular drug in small increments, such as when tapering or phasing one off of a drug to discontinue a therapy no longer needed-while also avoiding withdrawal adverse events.

Institutional settings whose principal purposes is not healthcare but which nonetheless provide healthcare, such as prison facilities, are another context in which consolidating and streamlining medications could provide organizational efficiencies as well as patient benefits.

Practitioners' options may also be broadened to more often prescribe drugs whose manufactured forms may be discontinued or unavailable. In some cases it could in effect ease drug shortages-whose causes include production delays, forecasting uncertainties, inventory planning issues, or manufacturing problems-by eliminating intermediary steps or bottlenecks in the supply chain. It can also address drugs whose mass-produced dosage levels are not optimal for a patient's weight, age (e.g. pediatrics), size, genetic profile, or condition severity-as mass-produced drug products have few dosing options, often based upon clinical trials which can have limited subject demographics (e.g. due to difficulty in patient recruitment, which has been notably documented regarding cancer drug trials). Further, custom dosing reduces demand for pill splitting-a practice which presents various safety and efficacy concerns, as has been advised against by the FDA.

Of interest, the increased throughput in drug discovery and validation that comes from using "API-into-Capsule" in current applications could prove complementary to expanding compounding as an alternative distribution route for such new drugs, free from some of the developmental hurdles of the mass-production route. Further, prospective implementation is enhanced by the fast-rising prevalence of various generic API and blend sources as drug patents expire (so-called "patent cliff"). Or as an alternative implementation strategy, production of suitable input cartridges could be incentivized by selectively granting exclusivity to particular drug manufacturer(s) and/or distributor(s).

While the text and drawings herein, including all content inherent therein, describe to and enable those of ordinary skill, such persons will also understand and appreciate the existence of enumerable variations, omissions, augmentations, combinations, and equivalents of specific device or method embodiments or examples. Many variations in forms and uses would occur to those in the art. Hence the foregoing description is not intended to be exhaustive or to limit inventive scope, and any references herein to the "invention" are intended in such a spirit. Elements or features of a particular embodiment or aspect of a device or method are generally not limited to that particular embodiment or aspect, but, where foreseeably applicable, are interchangeable, even if not specifically shown or described. These are not to be regarded as departures from any inventive concepts herein, and all such and other modifications are included within the scope of the same.

Following are clarifications and elaborations of select terminology. Definitions herein are not intended to be contrary to accepted definitions in the relevant field(s), so these clarifications serve chiefly to ensure adequate context.

For purposes herein, "automated" (and its variants) broadly includes any kind or extent of automation used in any capsule-filling machinery, such as the semi- or fully-automated microfilling machines already used in R&D. By contrast, "fully-automated" is a subset of "automated" which in the context of capsule-filling includes only those systems in which capsules are continuously fed during a machine's run without requiring manual handling.

For purposes herein, "encapsulated" and "capsule" (and their variants) refer broadly to any safely consumable (typically ingestible) form of containment suitable for placing a unit-dose of pharmaceutical material. (By contrast, the concept of "micro-encapsulation" refers instead to solid drug being encapsulated at the level of the particle, rather than to contain a unit dose). This is typically distinct from "tablets," which are binded and compacted blends, but if the containment is itself an excipient enclosure or substrate into or onto which drug is placed then it can be deemed a capsule rather than a tablet provided there is substantial structural envelopment of some kind. Capsule "shell" refers specifically to a capsule's material as distinguished from any contents it may contain. "Pill" is a relatively generic term which has come to encompass both capsules and tablets, depending upon the context.

For purposes herein, "compounding" (and its variants) refers to the practice of preparing prescription medication (which may be also combined with nonprescription medication or nutritional supplements) for particular patients. This typically requires not producing significantly more in number of a given unit-dose product than is needed for a given patient at a given time. Note that the term "dispensing" sometimes refers to a drug substance (e.g. API or blend) being dispensed to make a drug product (e.g. an occupied capsule), but in other contexts it can instead refer to inserting a finished drug product into a container or package for a particular patient. Depending upon the context, terms like "drug" or "medication" could refer to either a pharmaceutical substance itself or a product comprising it.

For purposes herein, "micro-dosing" or "precision microdosing" or "micro-filling" capability or technology (and its variants) refers to technological capability for dispensing sufficiently small and exact amounts of an API or formulation thereof as to render nonfunctional filler or bulker substantially unnecessary for measurement, handling, or production purposes. (Select excipients may still be desired for purposes such as pharmacokinetic or stability reasons, and solvent or lipid may still be useful for non-volumizing purposes.) Placement of material into capsules may be direct or multi-step (e.g. capsule-in-capsule) and content may range from beads to powder to semisolid to liquid (given appropriate features), yet microdosing herein does not necessitate using an intermediate substrate or sheet (although it could still be employed optionally). Note that this definition is different from another medical definition of "microdosing" that refers instead to administering sub-therapeutic amounts of a drug to a patient (e.g. to observe cellular-level effects).

For purposes herein, "capsule-filling" technology, equipment, etc. (and its variants) refers broadly to machinery for directly or indirectly placing pharmaceutical material into capsules.

What is claimed is:

1. A pharmaceutical polypill compounding system having automated micro-dosing capability, comprising:
    an interface configured to receive prescription information, said prescription information comprising patient-specific dose levels corresponding to respective drugs; and
    a capsule-filling machine adapted for patient-specific usage based on said prescription information, said capsule-filling machine comprising a dispenser for placing said drugs into capsules at said dose levels without manual weighing, said dispenser not being a fluid-drop generator, and said dispenser incorporating a micro-dosing technology that makes volume enhancement via inactive ingredient(s) unnecessary in order for said drugs to be dispensable at said dose levels:
    said systems being configured for producing polpills comprising solid particles, via dispensation of multiple different active pharmaceutical ingredients into the same capsules,via administration of mechanical disturbances to multiple respective dispensing heads each containing at least one of daid active pharmaceutical ingredients, said disturbances having a force or duration or frequency that gets adjusted according to gravimetric data obtained form recurring sensing of accumulating mass within said capsules during said dispensation.

2. The system of claim 1, wherein said dispenser is configured to dispense powder.

3. The system of claim 1, wherein said system is capable of dispensing a raw active pharmaceutical ingredient in a form neither processed nor formulated.

4. The system of claim 1, wherein said system is capable of dispensing particles comprising a functional coating.

5. The system of claim 1, wherein a supply of at least one drug(s) or inactive ingredient(s) is housed within a respective removable container(s) from which said supply can be dispensed by said system into capsules.

6. A process of utilizing a pharmaceutical polypill compounding system having automated micro-dosing capability, comprising:
    providing prescription information to a capsule-filling device, said prescription information comprising dose levels corresponding to respective drugs for a specific patient; and
    operating said device in producing for said patient a customized drug product or set thereof based on said prescription information, whereby said drugs are placed into capsules at essentially said dose levels in non-liquid form without manual measurement and without requiring that said drugs be enhanced by mass or volume relative to that of said drugs' respective active pharmaceutical ingredients;

said drug product being a polypill, a polypill being a pill comprising multiple distinct active pharmaceutical ingredients.

7. The process of claim 6, wherein said capsules are multi-compartment capsules.

8. The process of claim 6, wherein at least one of said drugs is placed into said capsules as microspheres.

9. The process of claim 6, wherein at least one of said distinct active pharmaceutical ingredients is pre-formulated.

10. The process of claim 6, wherein said process is directed toward reducing pill burden on patients having multi-drug regimens and/or toward reducing medication administration errors by healthcare personnel.

* * * * *